(12) United States Patent
Telleria Garay et al.

(10) Patent No.: US 11,738,155 B2
(45) Date of Patent: Aug. 29, 2023

(54) DEVICE FOR HANDLING A SYRINGE AND AUTOMATED DEVICE FOR PREPARING INTRAVENOUS MEDICATION COMPRISING SAID DEVICE FOR HANDLING A SYRINGE

(71) Applicant: KIRO GRIFOLS, S.L., Arrasate (ES)

(72) Inventors: Naiara Telleria Garay, Arrasate (ES); Asier Lizarriturri Martiarena, Arrasate (ES); Patxi Urtzelai Aranbarri, Arrasate (ES)

(73) Assignee: KIRO GRIFOLS, S.L., Arrasate (ES)

( * ) Notice: Subject to any disclaimer, the term of this patent is extended or adjusted under 35 U.S.C. 154(b) by 550 days.

(21) Appl. No.: 17/028,140

(22) Filed: Sep. 22, 2020

(65) Prior Publication Data
US 2022/0088318 A1 Mar. 24, 2022

(51) Int. Cl.
*A61M 5/32* (2006.01)
*A61J 3/00* (2006.01)
*B65B 55/02* (2006.01)

(52) U.S. Cl.
CPC .......... *A61M 5/3204* (2013.01); *A61J 3/002* (2013.01); *B65B 55/027* (2013.01); *A61M 2205/3327* (2013.01)

(58) Field of Classification Search
CPC .... B65B 55/027; B65B 69/00; A61M 5/3204; A61M 2205/3327; A61M 2005/3208; A61J 3/002
See application file for complete search history.

(56) References Cited

U.S. PATENT DOCUMENTS

2012/0318402 A1* 12/2012 Aguerre .................. B65B 3/003
141/2

FOREIGN PATENT DOCUMENTS

EP 2535034 A1 * 12/2012 .............. A61J 3/002
EP 2535034 A1 12/2012
(Continued)

OTHER PUBLICATIONS

KIRO Oncology; Robotic Compounding Systems; Oct. 2019; pp. 1-4 (Year: 2023).*
(Continued)

*Primary Examiner* — Bayan Salone
(74) *Attorney, Agent, or Firm* — Knobbe, Martens, Olson & Bear, LLP

(57) ABSTRACT

Device for handling a syringe and automated device for preparing intravenous medication comprising said device for handling a syringe The present invention discloses a device for handling a syringe, said syringe comprising a needle covered by a cap, said device comprising a main body which, in turn, comprises:
  a cap support comprising a housing for the cap of a needle, said housing being configured to hold said cap during removal and/or insertion of the needle from and/or into the cap by means of a linear movement;
  a device for joint removal of the cap and needle from the syringe by means of a rotation, comprising a slot defining two parallel faces spaced apart from each other and configured to interfere dimensionally with the cap of the syringe;
  at least one device for closing the syringe by means of a closed system transfer device (CSTD) or a cap, said device comprising a projection for fixing a support for said CSTD or cap, said support being replaceable and comprising a recess having a shape matching that of said projection and a housing of said CSTD or cap.

The present invention also discloses a support for a CSTD or a cap, a set comprising said device and at least one support for a CSTD or a cap, a system and a method for handling a syringe and two automated devices for preparing intravenous medication.

21 Claims, 11 Drawing Sheets

(56) References Cited

FOREIGN PATENT DOCUMENTS

| | | | | |
|---|---|---|---|---|
| EP | 2952171 A1 | * | 12/2015 | .............. A61J 3/002 |
| EP | 2952171 A1 | | 12/2015 | |
| EP | 2624802 B1 | * | 6/2016 | .............. A61J 3/002 |
| EP | 2624802 B1 | | 6/2016 | |
| WO | 2012172418 A2 | | 12/2012 | |
| WO | WO-2012172418 A2 | * | 12/2012 | .............. A61J 3/002 |

OTHER PUBLICATIONS

Grifolis, Inclusiv Compounding Portfolio; "KIRO Oncology Robotic Compounding System" Brochure in 4 pages. (Dec. 8, 2019).
Demonstration schedule for the "KIRO Oncology Robotic Compounding System" at the 54th ASHP Midyear Clinical Meeting & Exhibition in Las Vegas, Nevada on Dec. 8-12, 2019 in 7 pages.

\* cited by examiner

DEVICE FOR HANDLING A SYRINGE AND AUTOMATED DEVICE FOR PREPARING INTRAVENOUS MEDICATION COMPRISING SAID DEVICE FOR HANDLING A SYRINGE

FIELD OF THE INVENTION

The present invention relates to a device for handling a syringe, a support for a closed system transfer device or a cap for use with said device for handling a syringe, a set comprising said device for handling a syringe and at least one support for a closed system transfer device or a cap, a system for handling a syringe, an automated device for preparing intravenous medication that comprises said device for handling a syringe, an automated device for preparing intravenous medication comprising said system for handling a syringe and a method for handling a syringe.

BACKGROUND OF THE INVENTION

Traditionally, intravenous medication has been prepared manually by suitably qualified technicians. However, in recent years, automated devices have emerged for preparing intravenous medication with the aim of increasing patient safety by reducing possible dosing errors, etc., as well as the safety of the person responsible for preparing said medication, since this type of device notably reduces, or even eliminates, the exposure of personnel to substances that can be harmful to health.

Devices for the automated preparation of intravenous medication are disclosed, for example, in the European patent application publications EP 2535034 A1, EP 2624802 A1 and EP 2952171 A1.

The medication prepared in automated devices for preparing intravenous medication is usually a mixture of specific amounts of different base products and, in many cases, once said medication has been prepared, it is packaged in containers adapted to house it. The base products are usually stored in vials, from which a specific quantity is extracted for preparing the required medication. The vials or containers that house the necessary base products are usually placed in the device and said device handles them to prepare the required medication by handling said vials or containers in a specific order.

Oftentimes, the required medication is stored in syringes. These syringes will later be used by qualified medical personnel to administer the medication to the corresponding patient. To avoid loss of the medication contained in the syringe, as well as to ensure its sterility, among other reasons, it is advisable to close the syringes using caps or the like.

Traditionally, the closure of syringes has been carried out by means of caps, for example, of the Luer lock type. Although the use of caps for closing syringes gives very good results, it has the disadvantage of requiring the removal of the cap before the medication can be delivered to the patient, for example, by placing a needle. Continuing with the example, during the process of removing the cap and placing the needle, there is a risk of loss of the liquid contained in the syringe or the release of gases, vapours, etc. With the aim of limiting or eliminating said risk, among other advantages, what is known as a closed system transfer device (hereinafter, CSTD) has emerged, which is a transfer device that mechanically prevents the entry of contaminants into the system and the leakage or loss of the substance or its vapours out of the system.

The closure of the syringes using one of the different types of CSTDs currently available on the market (Phaseal®, Chemolock®, Onguard®, Tevadaptor®, Equashield®, etc.) makes it possible to avoid the aforementioned disadvantages of traditional caps. However, given that there are several types of CSTDs, each of them having a shape and characteristics different from the others, the use of CSTDs in automated and/or robotic systems, also has the disadvantage of being complicated, particularly in the case when more than one type of CSTD needs to be used.

Medication preparation in an automated device for preparing intravenous medication often requires the transfer of fluids from one container to another. This operation may, or even must, be carried out by using syringes equipped with their corresponding needle to introduce and/or remove liquid from one or more containers. However, despite possibly being necessary in specific phases of drug preparation, needles also carry a risk of accidentally puncturing or tearing other components, containers, etc. For this reason, it is especially advantageous for an automated device for preparing intravenous medication to be able to uncouple the needle from its corresponding syringe, as well as remove and/or insert the cap by means of which syringe needles are usually protected, since this increases the flexibility, as well as the operational safety, of the device. The presence of a cap protecting the needle eliminates the risks of accidentally tearing or puncturing other containers or elements of the automated intravenous preparation device and, above all, of puncturing the operator responsible for handling it, since it must be taken into account that, in addition to the risk of the puncture itself, the needle may be contaminated.

SUMMARY OF THE INVENTION

It is an object of the present invention to provide a device that allows the capping and uncapping of a syringe needle, that is, the removal and insertion of a needle cap, as well as the removal or uncoupling of the needle from the syringe and, in turn, also allows the closure of said syringe, increasing the productivity and reliability of the devices known in the prior art. Likewise, a further object of the present invention is to provide a device that, in addition to the above, also allows the use of various types of CSTDs for closing syringes. To this end, the present invention discloses a device for handling a syringe, said syringe comprising a needle covered by a cap, said device comprising a main body which, in turn, comprises:
- a cap support comprising a housing for the cap of a needle, said housing being configured to hold said cap during removal and/or insertion of the needle from and/or into the cap by means of a linear movement;
- a device for joint removal of the cap and needle from the syringe by means of a rotation, comprising a slot defining two parallel faces spaced apart from each other, configured to dimensionally interfere with the cap of the syringe;
- at least one device for closing the syringe by means of a closed system transfer device (CSTD) or a cap, said device comprising a projection for fixing a support for said CSTD or cap, said support being replaceable and comprising a recess having a shape matching that of said projection and a housing of said CSTD or cap.

Said device for handling a syringe is configured to be used preferably in an automated device for preparing intravenous medication. However, it may also be configured to be used in other types of devices, systems, etc.

Advantageously, the device for joint removal of the cap and needle from the syringe defines a longitudinal axis and is able to rotate thereabout. Alternatively, said device for joint removal of the cap and needle may lack the ability to rotate, in which case it should be the syringe, together with its cap and needle, which rotates with respect to said device for joint removal of the cap and needle.

In a preferred embodiment, said slot is perpendicular to the longitudinal axis of said device for joint removal of the cap and needle.

In an advantageous embodiment, said device for joint removal of the cap and needle from the syringe is connected to the main body of the device by means of a resilient element. Preferably, said resilient element comprises at least one spring.

Preferably, the cap support comprises a secondary slot arranged perpendicular to the cap housing and configured to receive a flange of the cap.

In a preferred embodiment, said cap housing is configured to dimensionally interfere with said cap.

Said secondary slot and the dimensional interference between the cap and its housing may be complementary or alternative characteristics.

Advantageously, the cap support comprises a sensor for detecting the presence of said cap. Among other advantages, said sensor makes it possible to verify that the cap remains in the support after removal of the needle, to verify that the cap comes out of the support after re-inserting the needle into it and/or to check that the housing of the cap support is empty and, therefore, ready to begin removal of a needle cap. Preferably, said sensor is a photocell.

Advantageously, said cap support is connected to the main body of the device by means of a resilient element. Preferably, said resilient element comprises at least one spring.

Advantageously, the projection of the device for closing the syringe comprises at least one holding element of the support for the closed system transfer device (CSTD) or the cap. Preferably, said projection comprises two opposing faces, each one comprising at least one holding element of the support for the closed system transfer device (CSTD) or the cap. Preferably, said holding element comprises a sphere or a hemisphere connected to said projection by means of a resilient element. Advantageously, said resilient element comprises a spring.

Advantageously, the at least one device for closing the syringe defines a longitudinal axis and has the ability to rotate thereabout. Alternatively, said device for closing the syringe may lack the ability to rotate, in which case it should be the syringe that rotates with respect to said device in order to close itself.

Preferably, the device for handling a syringe comprises a sensor for verifying the removal of the needle and the cap from the syringe.

Advantageously, the device for handling a syringe comprises a sensor for verifying the presence of a cap or a closed system transfer device (CSTD) on the syringe.

Advantageously, the device for handling a syringe comprises a motor that drives the at least one device for closing the syringe and the device for joint removal of the cap and needle by means of a transmission belt. Alternatively, the device for handling a syringe may comprise, for example, a motor for each device for closing the syringe and/or device for joint removal of the cap and needle.

According to another aspect of the present invention, a support for a closed system transfer device (CSTD) or a cap and for use with a device for handling a syringe as described above is also provided, said support comprising a body having a first and a second part, both parts being connected to each other, the first part comprising a recess having a shape matching that of a projection of a device for closing the syringe, and the second part comprising a housing for a closed system transfer device (CSTD) or a cap.

Preferably, the first and the second part of said support are connected to each other by at least one resilient element. Advantageously, said resilient element comprises a spring.

According to another aspect of the present invention, a set comprising a device for handling a syringe as described above and at least one support for a closed system transfer device (CSTD) or a cap as described above are also provided.

According to another aspect of the present invention, a syringe handling system comprising a syringe handling device as described above and a robotic arm configured to at least handle the syringe during removal and/or insertion of the needle from and/or into the cap, handle the syringe during joint removal of the cap and needle, and handle the syringe during closure of the cap by means of a closed system transfer system (CSTD) or a cap is also provided.

According to another aspect of the present invention, an automated device for preparing intravenous medication comprising a device for handling a syringe as described above is also provided.

According to another aspect of the present invention, an automated device for preparing intravenous medication comprising a system for handling a syringe as described above is also provided.

According to another aspect of the present invention, a method for handling a syringe comprising a needle and its cap is also provided, said method comprising the following steps:

introducing the cap, connected to its corresponding needle which, in turn, is connected to a corresponding syringe, into a housing of a cap support, said housing being configured to hold said cap during removal and/or insertion of the needle by means of a linear movement, removing the needle from its cap by means of a linear displacement of the syringe and its needle, introducing the needle into the cap located in the housing of the cap support by means of a linear displacement of the syringe and its needle, removing the cap, together with the needle and syringe, from the cap support, introducing the cap and its syringe into a slot of a device for joint removal of the cap and needle, removing the cap and the syringe together by means of a relative rotation between the cap and said slot of the device for joint removal of the cap and needle, closing the syringe by means of a relative rotation between the syringe and a closed system transfer device (CSTD) or a cap housed in a device for closing the syringe.

Preferably, said method comprises the step of verifying the presence of the cap in its housing by means of a sensor after removal of the needle by means of a linear movement.

Advantageously, said method comprises the step of verifying the joint removal of the cap and the syringe by means of a sensor.

Preferably, said method comprises the step of verifying the closure of the syringe by means of a sensor for detecting the presence of a closed system transfer device (CSTD) or a cap on said syringe.

Preferably, dosing of the medication in the syringe is carried out after removing the needle from its cap and before inserting said needle into said cap. However, said dosing of the medication may also be carried out in other steps of the present method.

In this document, the directions: horizontal, vertical, up, down, etc. are understood according to the normal working position of the device for handling a syringe, that is, with the longitudinal axis of said device for handling a syringe being perpendicular to the ground. If not indicated otherwise, in case of doubt, the directions are understood according to the positions of the different elements as shown in the figures that accompany this document.

BRIEF DESCRIPTION OF THE DRAWINGS

Several representative drawings of an exemplary embodiment of a device for handling a syringe, of a plurality of exemplary embodiments of a support for a closed system transfer device or a cap, and of an automated device for the preparation of intravenous medication, object of the present invention, are attached, by way of explanatory but non-limiting example, in order to provide a better understanding of the invention.

In the figures, identical or equivalent elements have been identified with identical numerals.

DETAILED DESCRIPTION OF THE PREFERRED EMBODIMENTS

Figure 1:
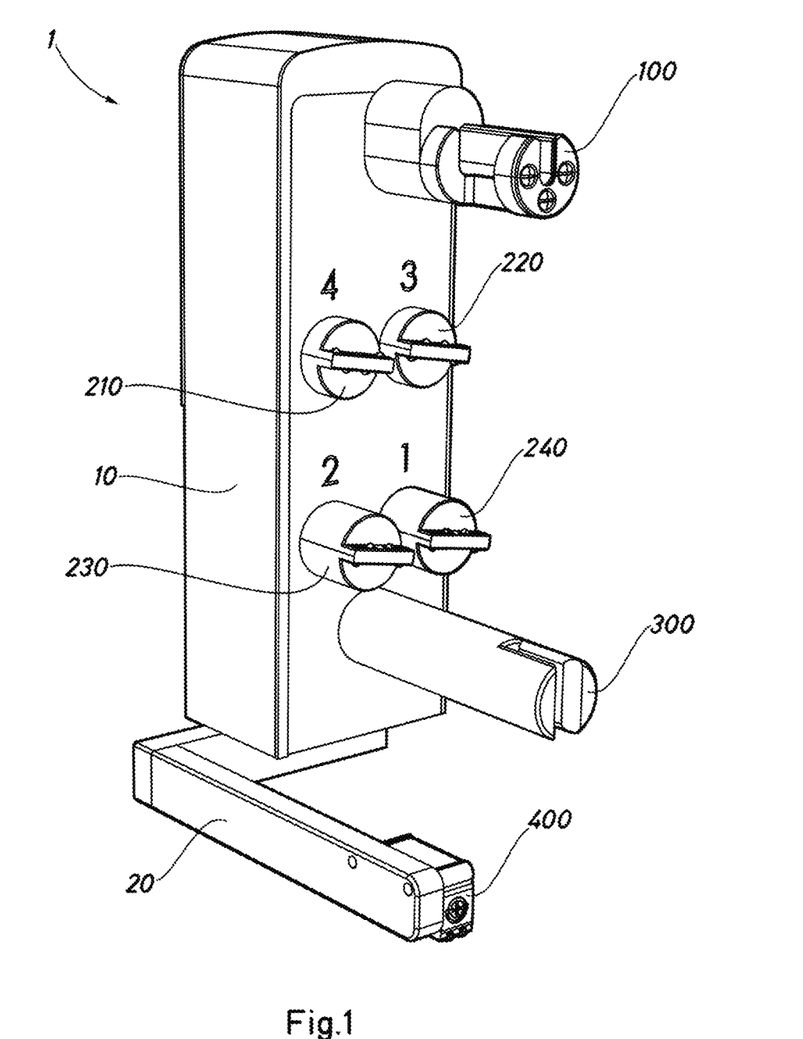
FIG. 1 is a perspective view of an exemplary embodiment of a device for handling a syringe according to the present invention.

FIG. 1 shows a perspective view of an exemplary embodiment of a device for handling a syringe according to the present invention. The device 1 of the exemplary embodiment shown in this figure comprises a main body 10 comprising on its front face a cap support 100, four devices 210, 220, 230, 240 for closing the syringe by means of a closed system transfer device (CSTD) or a cap, and a device 300 for joint removal of the syringe needle and its cap.

In the exemplary embodiment shown, the cap support 100 is located in the upper part of the front face of the main body 10 of the device 1, the device 300 for joint removal of the syringe needle and its cap is located on the lower part of said front face, and the devices 210, 220, 230, 240 for closing the syringe by means of a CSTD or a cap are located between them. More specifically, in this exemplary embodiment, the devices 210, 220, 230, 240 are distributed in the shape of a rectangle. However, in other embodiments, the distribution of the support 100 and the devices 210, 220, 230, 240, 300 may be different from that of the exemplary embodiment shown in this figure. Also, other embodiments may have a different number of devices 210, 220, 230, 240 for closing the syringe by means of a CSTD or a cap, such as one, two, three, five, etc.

The device 1 of the exemplary embodiment shown further comprises an arm 20 connected to its main body 10, said arm 20 comprising a sensor 400. Said sensor 400 is configured to verify the removal of the needle and the cap from the syringe, as well as to verify the presence of a cap or a CSTD on the syringe. In other embodiments, both functions may be carried out by two independent sensors, that is, one sensor for each function. Embodiments lacking said sensor 400 are also possible. In this case, it is assumed that the processes of inserting and removing the needle, etc. were correctly carried out.

Figure 2:
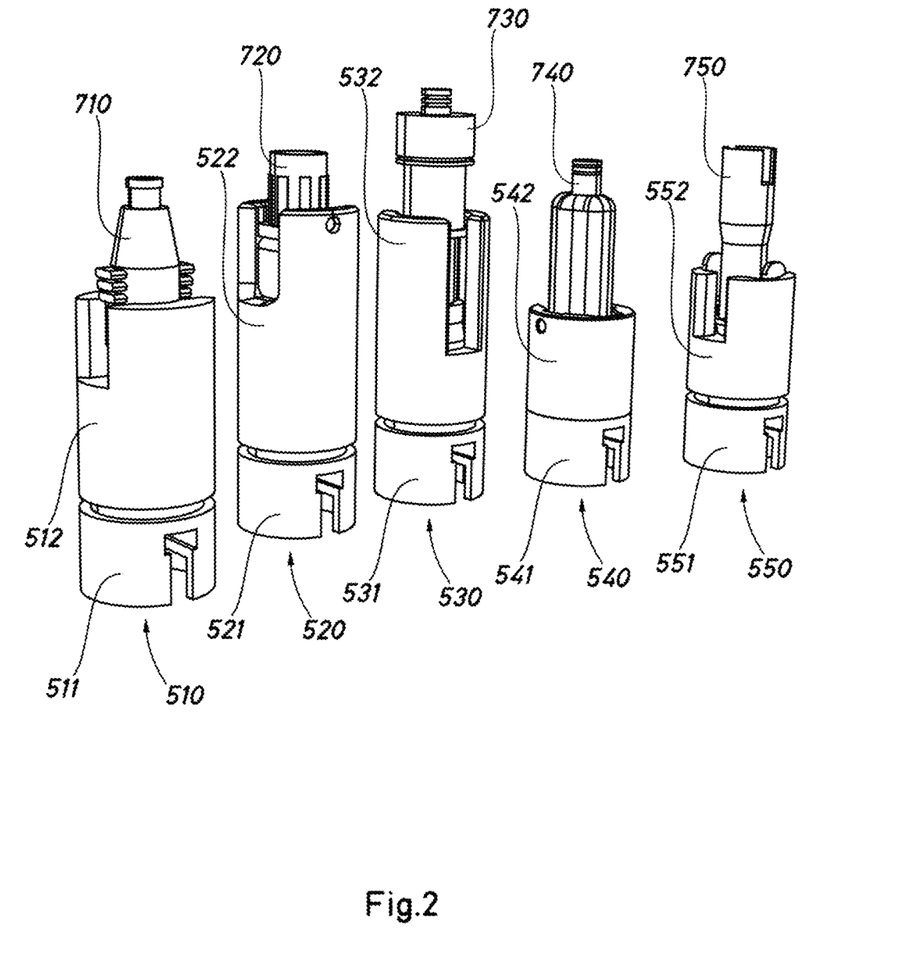
FIG. 2 is a perspective view of a plurality of exemplary embodiments of supports for a closed system transfer device (CSTD) or a cap according to the present invention.

FIG. 2 shows a perspective view of a plurality of supports for a closed system transfer device (CSTD) or a cap according to the present invention. Each support 510, 520, 530, 540, 550 is configured to be used with a different type of cap or CSTD (Phaseal®, Chemolock®, Onguard®, Tevadaptor®, Equashield®, etc.) 710, 720, 730, 740, 750.

Each support 510, 520, 530, 540, 550 comprises a first part 511, 521, 531, 541, 551 and a second part 512, 522, 532, 542, 552. The first part 511, 521, 531, 541, 551 is configured to be fixed to the corresponding device 210, 220, 230, 240 (see FIG. 1), while the second part 512, 522, 532, 542, 552 is configured to house the corresponding cap or CSTD 710, 720, 730, 740, 750.

The parts and functionality of the supports 510, 520, 530, 540, 550 will be described in detail below.

Figure 3:
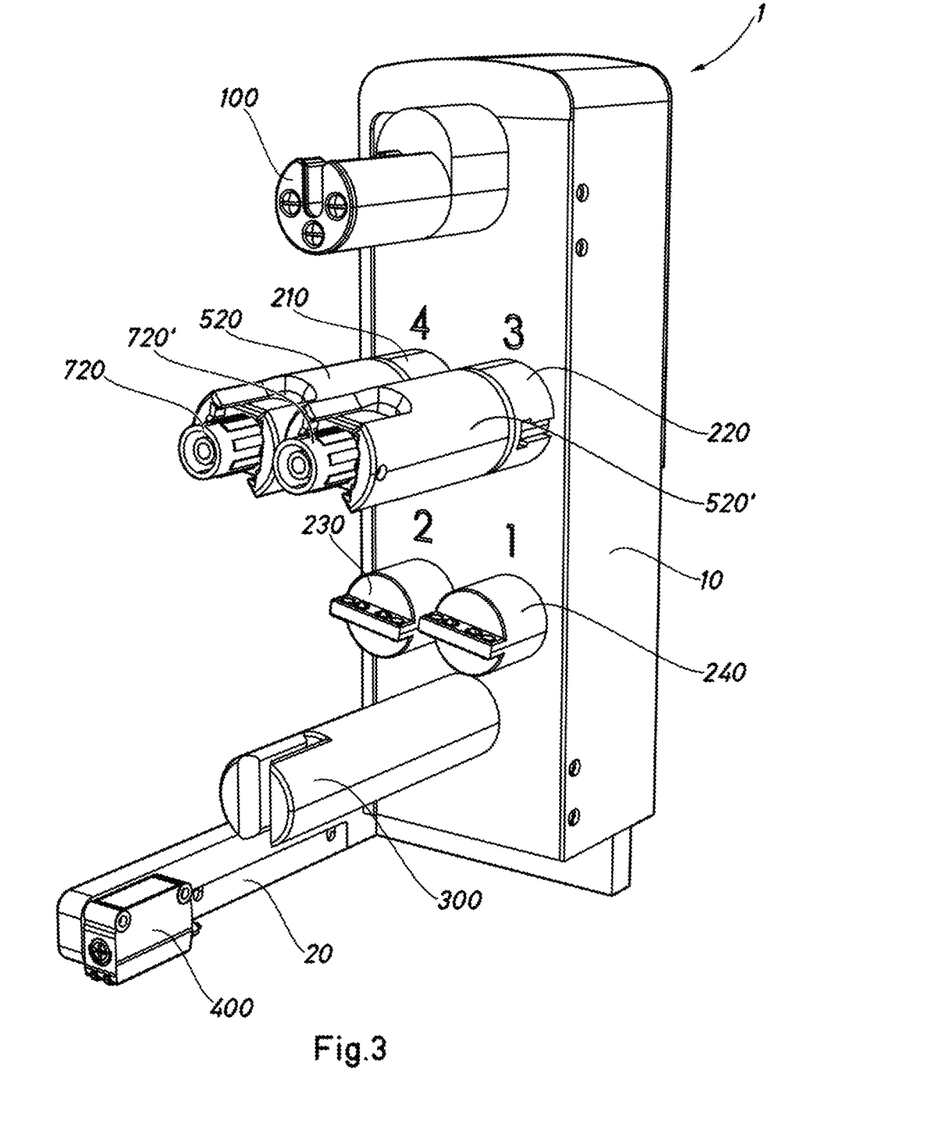
FIG. 3 is a perspective view of the exemplary embodiment of FIG. 1 equipped with two supports for a closed system transfer device (CSTD) or a cap according to the present invention.

FIG. 3 shows a perspective view of the device 1 of the exemplary embodiment shown in FIG. 1 having two supports 520, 520' arranged in their respective devices 210, 220. In turn, each support 520, 520' houses a corresponding cap or CSTD 720, 720'. FIG. 3 shows the device 1 illustrated in FIG. 1 and its different components from another point of view.

Figure 4:
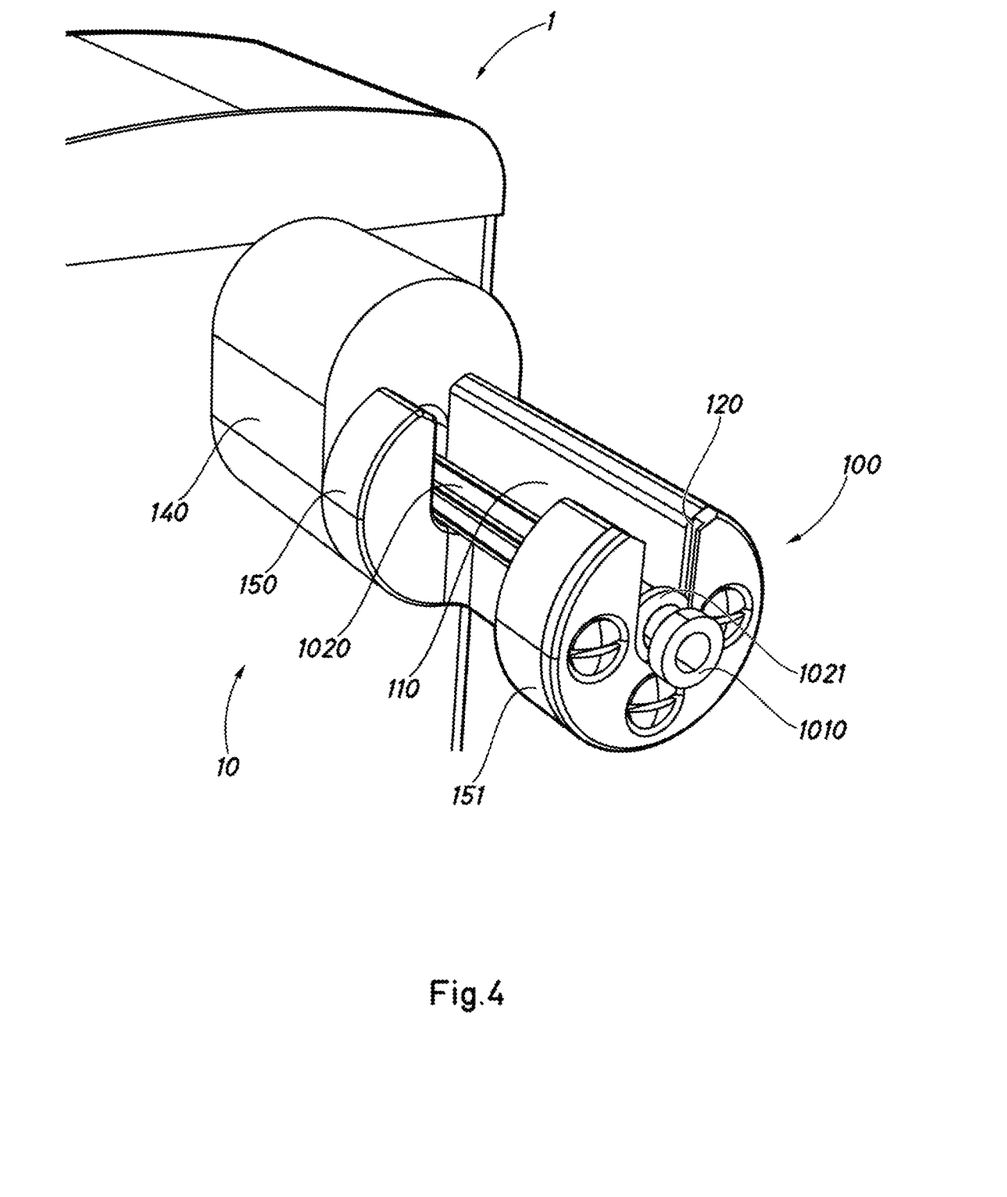
FIG. 4 is a perspective view of the cap support of the exemplary embodiment of FIG. 1.

FIG. 4 shows a perspective view of the cap support 100 of the device 1 shown in FIG. 1. This figure shows how the cap support 100 comprises a housing 110 for the cap 1020 of the needle 1010 of a syringe (not shown). Said housing 110 for the cap may also be referred to as the main housing 110. Said housing 110 for the cap or main housing may be dimensioned to interfere dimensionally with the cap 1020 of the needle 1010. In the exemplary embodiment shown, the support 100 comprises a secondary slot 120 arranged perpendicular to the housing 110 for the cap 1020 and configured to receive a flange 1021 of said cap 1020 of the needle 1010. The interference created between the secondary slot 120 and the flange 1021 of the cap 1020 prevents said cap 1020 from being axially displaced when the syringe 1010 is removed and/or inserted by means of an axial movement thereof. The secondary slot 120 may supplement, or even replace, the dimensional interference between the housing 110 for the cap 1020 and the cap 1020. Embodiments in which, for example, the dimensional interference between the housing 110 for the cap 1020 and the cap 1020 offer sufficient resistance to axial displacement, may dispense with the secondary slot 120 or the like. Alternatively, embodiments in which the secondary slot 120 offers an interference between itself and the cap 1020, and more specifically its flange 1021, which offers sufficient resistance to axial displacement, may dispense with the dimensional interference between the support 110 for the cap 1020 and the cap 1020, or other types of holding means of said cap 1020 during removal and/or insertion of needle 1010 by means of a linear movement.

In the exemplary embodiment shown, the cap support 100 comprises a base 140 to which a part comprising two bases 150, 151 of substantially circular shape is connected. Each base 150, 151 comprises a slot aligned with the other to define the housing 110 for the cap 1020. Said support 100 may be deemed to have a cradle-like shape.

The support 100 of the exemplary embodiment shown is connected through its base 140 to the main body 10 of the device by means of springs 130 (see FIGS. 5 and 6) so that the connection between said support 100 and said device 1 is not rigid. The connection by springs 130 allows the support 100 to be floating relative to the device 1, thus allowing the absorption of forces exerted on the support or the cap 1020 and its syringe 1010 during the operation thereof, among other advantages. In other embodiments, said springs 130 may be replaced by any other suitable resilient means.

Figure 5:
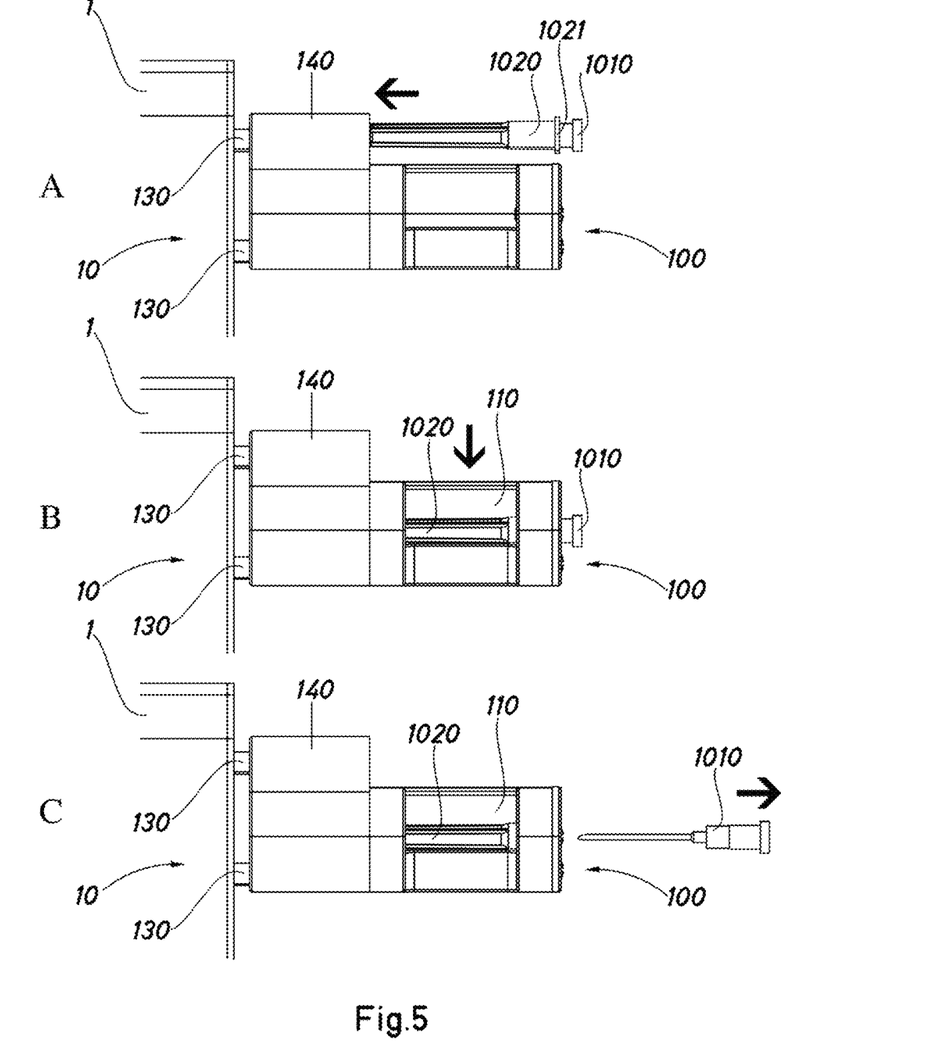
FIG. 5 is a side view illustrating the process of removing the cap from a syringe using the exemplary embodiment of FIG. 1.
Figure 6:
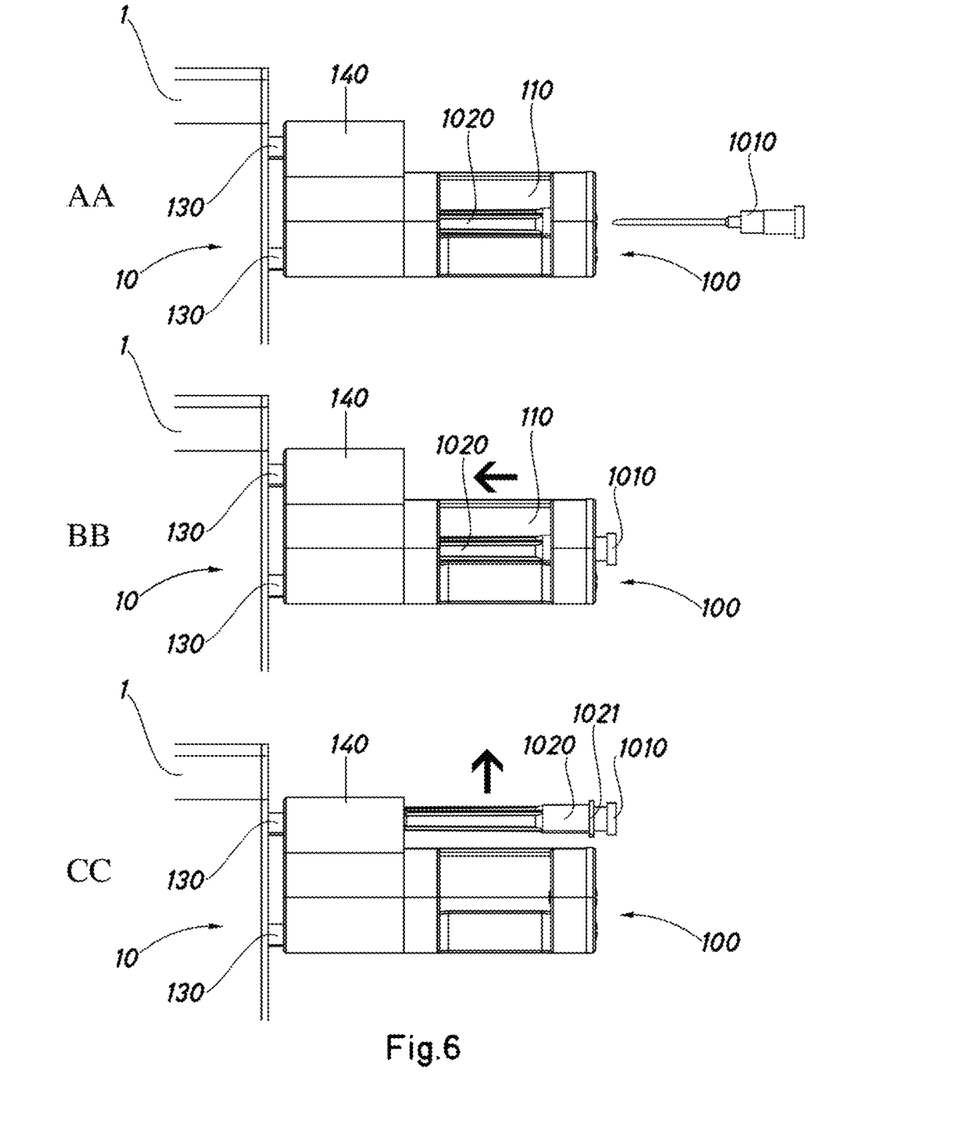
FIG. 6 is a side view illustrating the process of inserting the needle of a syringe into a cap using the exemplary embodiment of FIG. 1.

FIGS. 5 and 6 show a side or profile view of the process of removing and inserting the cap of a syringe needle, respectively, by means of the device 1 shown in FIG. 1. These figures clearly show the pairs of springs 130 connecting the base 140 of the support 100 of the cap 1020 to the main body 10 of the device 1.

FIG. 5 illustrates in three steps A, B, C the process of removing the cap 1020 from the syringe needle 1010. In the first step A, the cap 1020 and syringe needle 1010 (not shown) are placed on top of the housing 110 for the cap 1020 and aligned with it. Additionally, in the exemplary embodiment shown, said cap 1020 is pushed until it abuts the base 140. In this way the flange 1021 of the cap 1020 is aligned with the secondary or auxiliary slot 120 (see FIG. 4) of the device 1 of the exemplary embodiment shown.

Once the cap 1020, and consequently the needle 1010, are aligned with the housing 110 for the cap 1020 and the secondary slot 120, the second step B consists of lowering the syringe (not shown) together with its cap 1020 and needle 1010 until said cap 1020 abuts the housing 110 for the cap 1020.

After completion of the second step B, the third step C consists of axially displacing the syringe (not shown) and its needle 1010 in the opposite direction to the device 1 so that the needle 1010 comes out of the cap 1020. Due to the interference between the flange 1021 of the cap 1020 and the auxiliary slot 120, as well as the possible dimensional interference between the cap 1020 and the housing 110 for the cap 1020, it is possible to remove the needle 1010 from the cap 1020 without the latter being displaced.

Once the needle 1010 has been removed from the cap 1020, the processes required for preparing the medication can be carried out.

In the exemplary embodiment shown, the support 100 comprises a sensor (not shown) to verify the presence of the needle cap 1020. In this way, in case the cap 1020 comes out of its housing 110 due to some error, an alarm or error signal could be emitted and the medication preparation process could even be stopped. Another advantage of the presence of said sensor is that it makes it possible to ensure that the needle 1010 of the syringe is free, in other words, if the cap 1020 is on the support 100, it cannot be covering the needle 1010, and therefore, said needle 1010 is ready to be used in the medication preparation process.

FIG. 6 illustrates in three steps AA, BB, CC the process of introducing the needle 1010 of the syringe (not shown) into the cap 1020.

Upon completion of the processes for preparing the medication in which it is necessary to use the needle 1010 of the syringe (not shown), it is advisable to put the needle 1010 back into its cap 1020 to avoid damaging it and avoid tearing, piercing, ripping, etc. any of the equipment or containers inside the automated device for preparing intravenous medication in which, preferably, the device 1 is installed. It is also advisable to put the needle 1010 back inside its cap 1020 to avoid tears and/or breakage of the refuse bags or waste containers in which used needles 1010 are deposited, as well as to avoid accidents (especially punctures) to the personnel responsible for emptying said refuse bags or containers where used needles 1010 are deposited.

The first step AA for the introduction of the needle 1010 into its cap 1020 consists of aligning said needle 1010 with its cap 1020.

Once the needle 1010 is aligned with its cap 1020, the second step BB consists of axially moving the needle 1010 until it is introduced inside the cap 1020 so that said cap 1020 interferes dimensionally with the cone of the needle 1010, or the like, and both are connected.

The third step CC in the process of introducing the needle 1010 into its cap 1020 consists of lifting, or radially displacing, the syringe (not shown) together with its needle 1010 and its cap 1020 along its housing 110 until the syringe, its needle 1010 and its cap 1020 are released from the support 100.

The springs 130 that connect the base 140 of the support 100 to the main body 10 of the device 1 allow small shocks, excessive forces, misalignments, etc. to be absorbed that may occur during the process of removing and inserting the cap 1020 and which, if not cushioned or absorbed, could damage the needle 1010, the cap 1020, the syringe or even the support 100.

Figure 11:
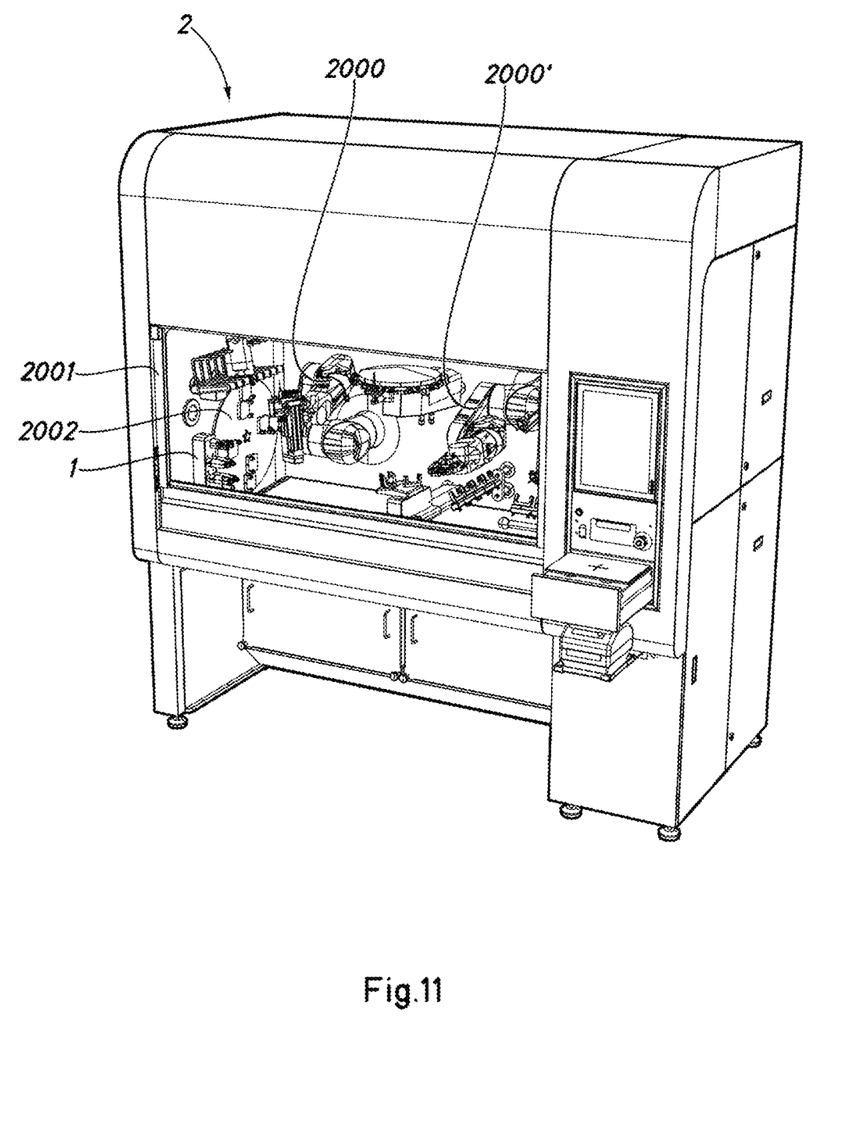
FIG. 11 is a perspective view of an exemplary embodiment of an automated device for preparing intravenous medication according to the present invention.

The processes for removing and introducing the cap 1020 illustrated in FIGS. 5 and 6, respectively, in the exemplary embodiment shown, are carried out by a robotic arm or the like of an automated device for preparing intravenous medication (see FIG. 11). However, they could also be carried out by a suitably qualified operator.

In the exemplary embodiment shown, the procedure followed in the process of introducing the syringe 1010 into the cap 1020 is the one described in the European patent application publication EP 3176540 A1, although other embodiments may follow different procedures.

Figure 7:
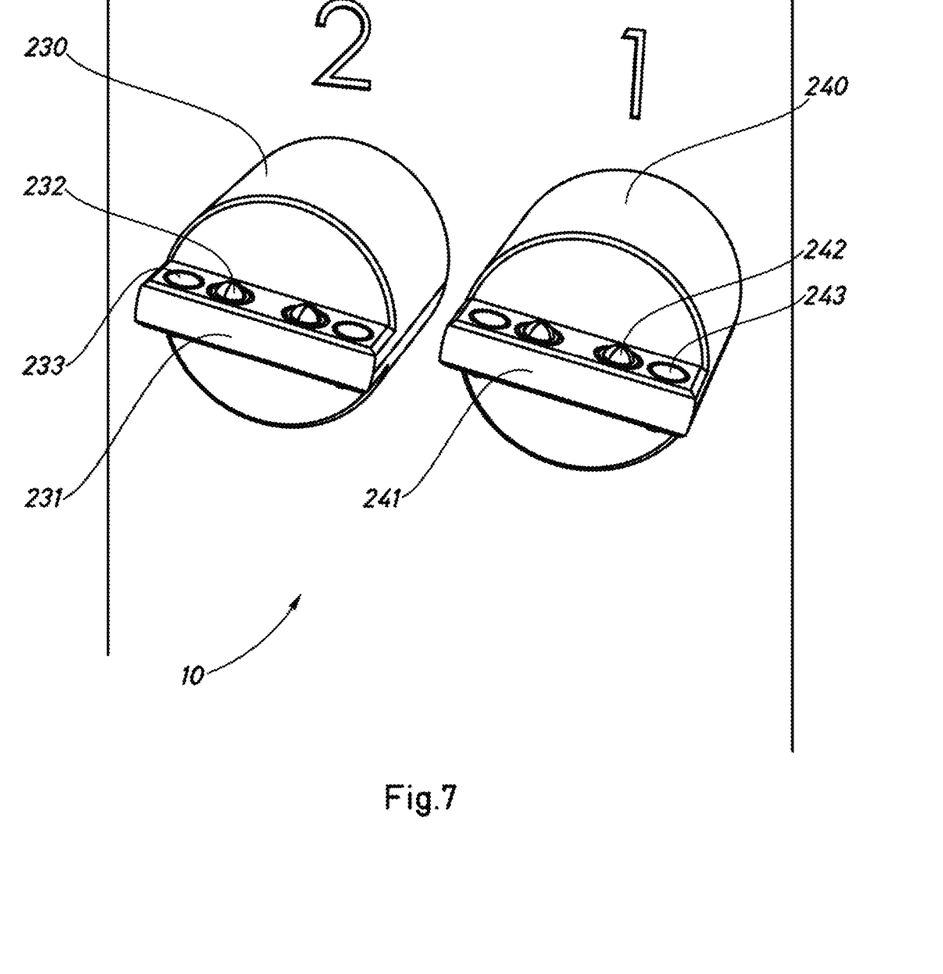
FIG. 7 is a perspective view of two devices for closing the syringe by means of a closed system transfer device (CSTD) or a cap of the exemplary embodiment of FIG. 1.

FIG. 7 shows a perspective view of two of the devices 230, 240 for closing the syringe by means of a closed system transfer device (CSTD) or a cap of the device 1 shown in FIG. 1. As can be seen, in the exemplary embodiment shown, the device 230, 240 is substantially cylindrical in shape and comprises at one of its ends, the one that is not connected to the device 1, a projection 231, 241 having a shape matching that of a recess of a support for a CSTD or a cap (see, for example, FIG. 8). In the exemplary embodiment shown, the flat and parallel faces of the projection 231, 241 and the corresponding recess of the support (see, for example, FIG. 8) allow the rotary movement of the device 230, 240 to be transmitted efficiently to the corresponding support which, in turn, will be responsible for transmitting it to the corresponding CSTD or cap. To increase the fixation of the support to the device 230, 240, in the exemplary embodiment shown, the projection 231, 241 comprises holding elements. More specifically, the projection 231, 241 of the device 230, 240 comprises a plurality of spheres 232, 242 connected to the projection 231, 241 by means of a spring or the like. Said spheres 232 are configured to fit into matching recesses within the recess of the corresponding support for the CSTD or cap. Said spheres 232, 242 may also be hemispheres or have any other suitable shape. In order to further increase the fixation between the support and the device 230, 240, in the exemplary embodiment shown, the projection 231, 241 additionally comprises a plurality of holes 233, 243 configured to allow a particular sphere or hemisphere, located in the corresponding recess of the support, to fit thereinto.

Figure 8:
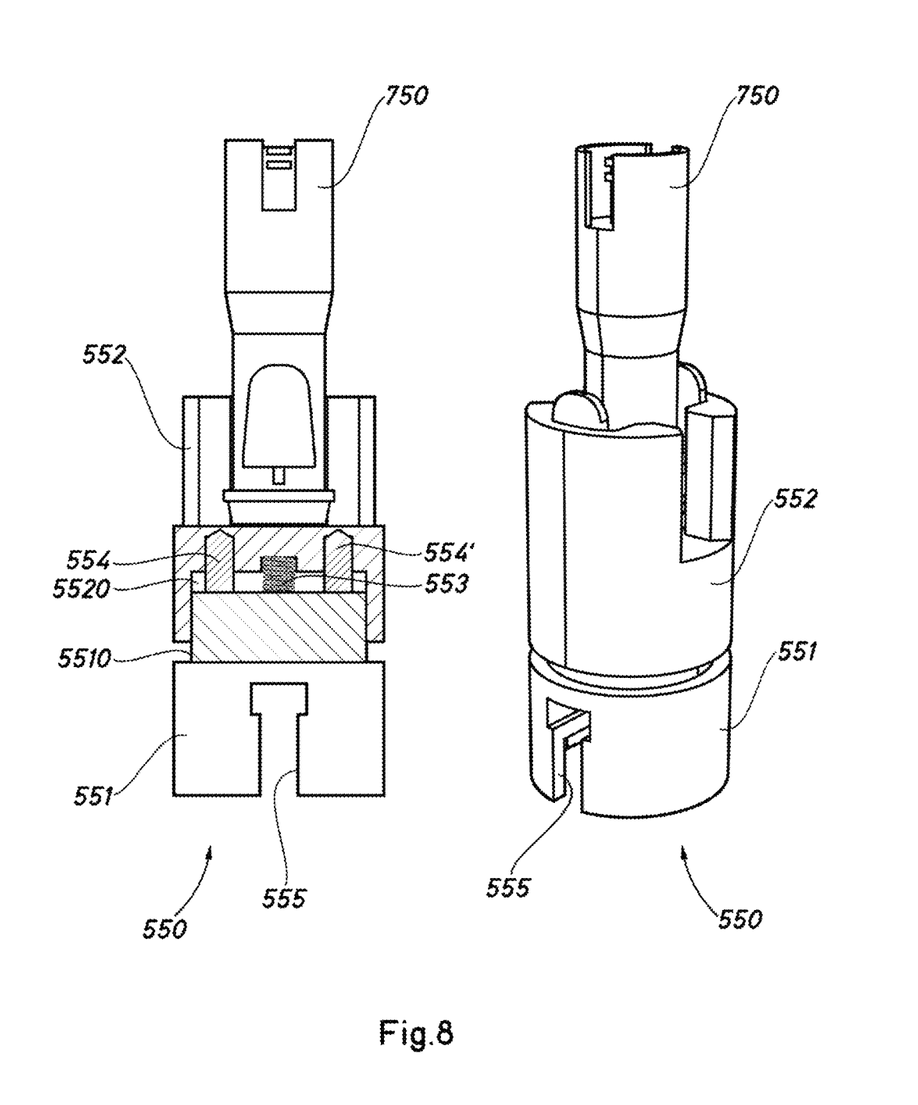
FIG. 8 is a perspective view and a longitudinal sectional view of an exemplary embodiment of a support for a closed system transfer device (CSTD) or a cap according to the present invention.

FIG. 8 shows a perspective view and a longitudinal sectional view of an exemplary embodiment of a support for a closed system transfer device (CSTD) or a cap according to the present invention. The support 550 of the exemplary embodiment shown comprises a first part 551 and a second part 552. As can be seen in the sectional view, both parts 551, 552 are connected by at least one spring 553. Said connection between parts 551, 552 by resilient means allows the second part 552 to be floating in relation to the first part 551, thus allowing, among other advantages, the support 550 to be able to absorb excessive forces exerted on the CSTD 750 or the cap, or on the second part 552.

The support 550 shown also comprises a pair of screws 554, 554' that limit the displacement between the first part 551 and the second part 552 of the support 550 and guide the movement between both parts. In the exemplary embodiment shown, the movement between both parts 551, 552 is also guided by the fitting between a projection 5510 of the first part 551 and a recess 5520 in the second part 552. Additionally, the pair of screws 554, 554' also helps to transmit the movement of the first part 551 to the second part 552, the corresponding device 210, 220, 230, 240 (see, for example, FIG. 1) being responsible for transmitting a rotary movement to the support 550 which, in turn, is responsible for transmitting said rotary movement to the CSTD 750 or cap.

In the exemplary embodiment shown, the support 550, and more specifically, the first part 551 thereof, comprises a recess or slot 555 having a shape matching that of the projection 231, 241 of the corresponding device 230, 240 (see FIG. 7). In this way, the support 550 is fixed to the corresponding device 230, 240 and is capable of transmitting the rotary movement of said device 230, 240 to the particular CSTD 750 or cap. In the exemplary embodiment shown, said rotary movement is used for fixing said CSTD 750 or cap to the corresponding syringe for its closure.

As can be seen, in the exemplary embodiment shown, the CSTD 750 or cap is housed in a recess formed in the second part 552 of the support 550 that has a shape matching that of the CSTD 750 or cap that it is intended to house.

After closing the syringe by means of the corresponding CSTD 750 or cap, the syringe (not shown) may be placed in the detection field of the sensor 400 (see FIGS. 1 and 3) to verify the presence of the cap or CSTD on the syringe. If the sensor 400 verifies the presence of the cap or CSTD on the syringe, said syringe can already be considered as finished and can be supplied to the corresponding operator or stored to be later supplied together with other syringes. In embodiments lacking the sensor 400, it is assumed that the cap or CSTD has been correctly placed by the support 510, 520, 530, 540, 550 and the corresponding device 210, 220, 230, 240 (see FIGS. 1 to 3).

Figure 9:
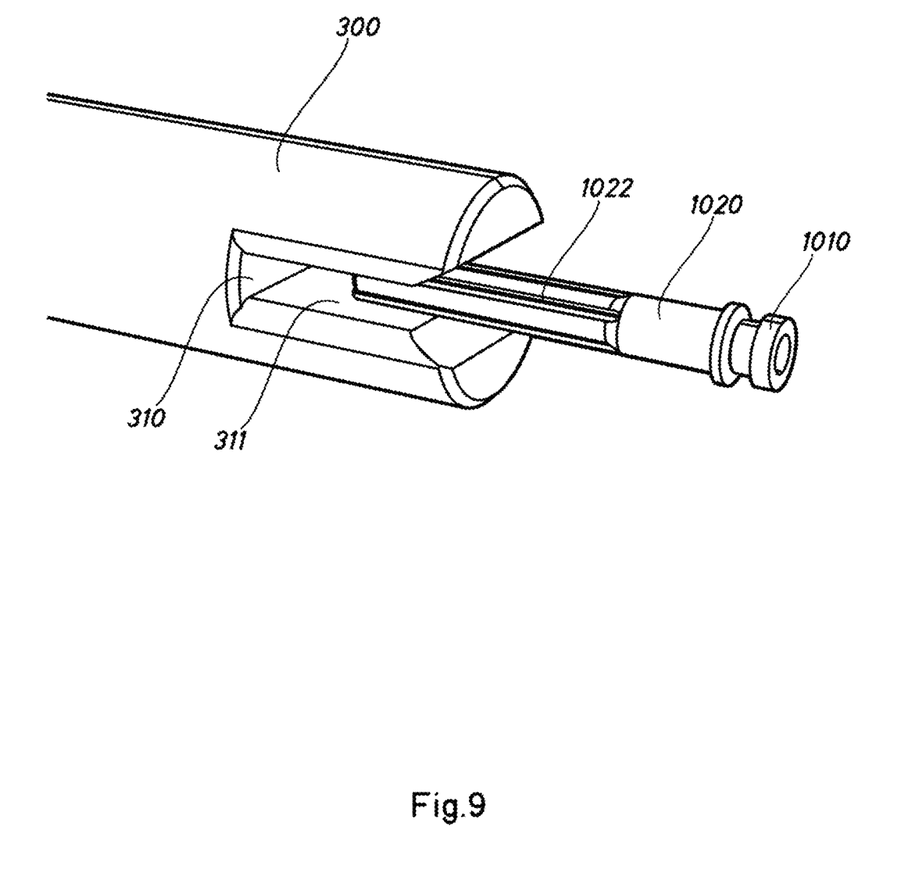
FIG. 9 is a perspective view of the device for joint removal of the cap and needle from the syringe of the exemplary embodiment of FIG. 1.

FIG. 9 shows a perspective view of the device 300 for joint removal of the cap and its needle from the device 1 shown in FIG. 1. Said device 300 comprises a slot 310 defined by two parallel faces 311. The separation or distance between both faces 311 is such that it allows the cap 1020 of the needle 1010 to interfere dimensionally with said faces. In the exemplary embodiment shown, the cap 1020 has a plurality of external ribs 1022, in this case, four, distributed in the shape of an X. The cap 1020 and its ribs 1022, as well as the separation between the faces 311 of the slot 310 of the device 300 are dimensioned so that in a specific angular position of the cap 1020, the latter can be introduced into the slot 310 and that, after varying the relative angular position between the cap 1020 and the slot 310, either after the rotation of the cap 1020 or the rotation of the slot 310, said cap 1020 and said slot 310 interfere dimensionally, and more specifically, the ribs 1022 of the cap 1020 dimensionally interfere with the faces 311 of the slot 310. In the case of the exemplary embodiment shown, the device 300 is responsible for rotating.

If the device 300 continues to rotate while holding the syringe (not shown) in a fixed position when the cap 1020 dimensionally interferes with the slot 310, the device 300 uncouples the cap 1020 and needle 1010 from the syringe (not shown). Although the device 300 carries out the action on the cap 1020, the latter is connected to the cone of the needle 1010, by dimensional interference in the exemplary embodiment shown, so that the rotation exerted on the cap 1020 is transferred to the needle 1010 until the needle is unscrewed or uncoupled from the syringe (not shown). To keep the syringe in a fixed position, it is preferably held by an arm. In the exemplary embodiment shown, said arm is a robotic arm (see FIG. 11), although it could also be the arm of an operator.

In the exemplary embodiment shown, the device 300 is connected to the device 1 by means of resilient means that allow potential misalignments, excess pressure, etc. to be absorbed when the syringe and, more specifically, its cap 1020, approaches and inserts into the slot 310. Specifically, in the exemplary embodiment shown, said resilient means are springs.

After removal of the cap 1020 and the needle 1010 from the corresponding syringe (not shown), said syringe may be placed in the detection field or detection zone of the sensor 400 to verify the correct removal of the cap 1020 and the needle 1010 from the syringe, and confirm that said syringe is ready to be closed by means of a cap or CSTD using a device 210, 220, 230, 240 and the corresponding support 510, 520, 530, 540, 550.

After removal of the cap 1020 and the needle 1010, both can fall by gravity from device 300 into a waste container or the like. In other embodiments, a robotic arm (see FIG. 10) may be configured, for example, to remove said cap 1020 and needle 1010 from device 300 and drop them into said waste container. Said robotic arm (see FIG. 10) may also be configured to grasp said cap 1020 and needle 1010, remove them from device 300 and transfer them into a waste container or the like.

The process followed by a syringe containing a final product or medication, that is to say, which is ready for administration to the patient, has been previously described. However, the syringe handling device 1 also serves to handle transfer syringes, that is, syringes that are used to transfer substances between vials, bags, etc. but are not intended for administration to a user or patient. In the latter case, after use, the corresponding cap 1020 may be placed on the needle 1010 following, for example, the procedure illustrated in FIG. 6, and, subsequently, the syringe may be discarded by depositing it in a corresponding waste container. To avoid accidents, tears, punctures, etc. it is highly recommended to introduce the syringe needle into its cap before disposing of said syringe.

Figure 10:
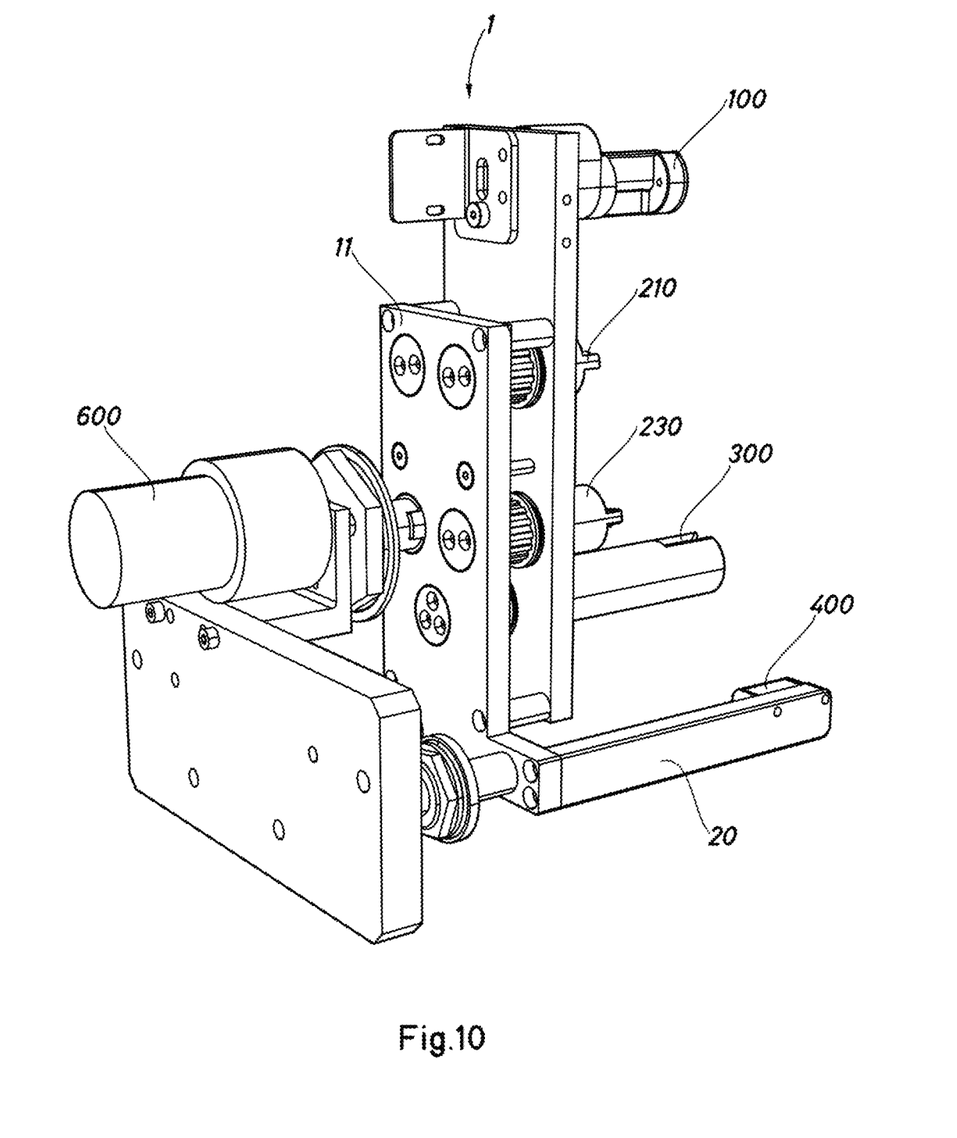
FIG. 10 is a rear perspective view of the exemplary embodiment of FIG. 1 without its outer casing.

FIG. 10 shows a rear perspective view of the device 1 shown in FIG. 1, but without the casing that covers the main body 10 (see FIG. 1), thus making it possible to see the internal structure 11 of said main body 10. In addition to allowing some elements of the device 1 to be seen from a point of view different from that of the figures described above, this figure allows the motor 600 to be seen which is responsible for operating the devices 210, 220, 230, 240, 300 and, more specifically, responsible for making them rotate about its own longitudinal axis. Said rotation of the devices 210, 220, 230, 240, 300 may be clockwise and/or counterclockwise.

In the exemplary embodiment shown, a single electric motor 600 is responsible for driving the devices 210, 220, 230, 240, 300 by means of a toothed belt transmission (not shown). However, in other embodiments, the actuation of the different devices may be carried out by other types of transmission. It is also possible that other embodiments comprise more than one motor for driving the devices, for example, one motor for two devices 210, 220, 230, 240, 300, or even that each device 210, 220, 230, 240, 300 comprises its own motor, thus achieving greater independence in the operation of the devices 210, 220, 230, 240, 300, and consequently, of the device 1 for handling a syringe that comprises them.

FIG. 11 shows a perspective view of an exemplary embodiment of an automated device for preparing intravenous medication according to the present invention. As can be seen, the automated device 2 for preparing intravenous medication shown in this figure comprises two robotic arms 2000, 2000'. Said robotic arms 2000, 2000' are responsible for handling the syringes, vials, etc. used to prepare intravenous medication. The device 2 comprises a sash window 2001 that allows access to the workspace of the device 2. Said window 2001 is configured to maintain the required cleanliness and sterility conditions inside the device once closed. Furthermore, said window 2001 is made of transparent or translucent material to allow the supervision of the operations carried out by the device 2 from the outside thereof by a duly qualified operator.

In the exemplary embodiment shown, the automated device 2 for preparing intravenous medication comprises a device 1 for handling a syringe. To maximize the productivity of the robots 2000, 2000' and the rest of the elements of the device 2, the device 1 is located in the lower zone of the left-hand side (from the point of view of FIG. 11) between the carousel 2002 and the sash window 2001. When in this position, the robotic arm or robot 2000 is responsible for interacting with said device 1.

In the exemplary embodiment shown, when the device 2 is not in operation and the sash window 2001 is open, a duly qualified operator is responsible for placing a plurality of empty syringes with their corresponding needle and cap in the carousel 2002. Said syringes, together with their needle and cap located in the carousel 2002, will later serve to feed the device 2, the robotic arm 2000 being responsible for removing the corresponding syringe from the carousel 2002 and starting the work required with said syringe.

With reference to the figures described above, in the device 2 of the exemplary embodiment shown in FIG. 11, the robotic arm 2000 is responsible for removing and/or putting on the cap 1020 of the syringe 1010 by means of the cap support 100 following the procedures illustrated in FIGS. 5 and 6. After the preparation of the medication by the device 2, the robotic arm 2000 is responsible for putting the cap 1020 on the needle 1010 to later transfer the syringe together with its needle 1010 and its cap 1020 to the device 300 for joint removal of the cap 1020 and the needle 1010 from the syringe, where both are removed. After this step, the robotic arm 2000 is responsible for closing the syringe with a cap or a CSTD using one of the devices 210, 220, 230, 240 equipped with the corresponding support 510, 520, 530, 540, 550 which, in turn, houses the particular cap or CSTD 710, 720, 730, 740, 750. When the syringe is already properly closed using its corresponding cap or CSTD 710, 720, 730, 740, 750, the device 2 can proceed to deliver said syringe to the corresponding operator or store it inside for a subsequent delivery. This is the case when the syringe comprises a final product or medication. As indicated above, in the case that the syringe is a transfer syringe, that is, a syringe to be used for the transfer of fluids between different containers (vials, bags, etc.) for preparing a medication, said transfer syringe may be disposed of by placing it in a corresponding waste container after inserting the needle 1010 into its corresponding cap 1020. Disposing of a needle 1010 and/or a syringe together with its needle 1010 without capping it with its corresponding cap 1020 could cause serious accidents (punctures, breaks, etc.).

Although the invention has been presented and described with reference to embodiments thereof, it will be understood that these are not limiting of the invention, so that multiple variable design details or other details that may be obvious to a person skilled in the art after interpreting the subject matter disclosed in the present description, claims and drawings are possible. In particular, in principle and unless explicitly stated otherwise, all the characteristics of each of the different embodiments and alternatives shown and/or suggested can be combined with each other. Thus, all variants and equivalents will be included within the scope of the present invention if they can be considered to be within the broader scope of the following claims.

What is claimed is:

1. A device for handling a syringe, said syringe comprising a needle covered by a cap, said device comprising a main body which, in turn, comprises:
   - a cap support comprising a housing for the cap of a needle, said housing being configured to hold said cap during removal and/or insertion of the needle from and/or into the cap by means of a linear movement;
   - a device for joint removal of the cap and needle from the syringe by means of a rotation, comprising a slot defining two parallel faces spaced apart from each other and configured to interfere dimensionally with the cap of the syringe;
   - at least one device for closing the syringe by means of a closed system transfer device (CSTD) or a cap, said device comprising a projection for fixing a support for said CSTD or cap, said support being replaceable and comprising a recess having a shape matching that of said projection and a housing of said CSTD or cap.

2. The device according to claim 1, wherein the device for joint removal of the cap and needle from the syringe defines a longitudinal axis and has the ability to rotate thereabout.

3. The device according to claim 2, wherein said slot is perpendicular to the longitudinal axis of said device for joint removal of the cap and needle.

4. The device according to claim 1, wherein said device for joint removal of the cap and needle from the syringe is connected to the main body of the device by means of a resilient element.

5. The device according to claim 1, wherein the cap support comprises a secondary slot arranged perpendicular to the housing for the cap and configured to receive a flange of the cap.

6. The device according to claim 1, wherein said housing for the cap is configured to dimensionally interfere with said cap.

7. The device according to claim 1, wherein the cap support comprises a sensor for detecting the presence of said cap.

8. The device according to claim 7, wherein said sensor is a photocell.

9. The device according to claim 1, wherein said cap support is connected to the main body of the device by means of a resilient element.

10. The device according to claim 1, wherein the projection of the device for closing the syringe comprises at least one holding element of the support for the closed system transfer device (CSTD) or the cap.

11. The device according to claim 10, wherein said projection comprises two opposing faces, each one comprising at least one element for holding the support for the closed system transfer device (CSTD) or the cap.

12. The device according to either claim 10, wherein said holding element comprises a sphere or a hemisphere connected to said projection by means of a resilient element.

13. The device according to claim 1, wherein the at least one device for closing the syringe defines a longitudinal axis and has the ability to rotate thereabout.

14. The device according to claim 1 further comprising a sensor for verifying the removal of the needle and cap from the syringe.

15. The device according to claim 1 further comprising a sensor for verifying the presence of the cap or the closed system transfer device (CSTD) on the syringe.

16. A support for a closed system transfer device (CSTD) or a cap and for use with the device according to claim 1, comprising a body with a first part and a second part, wherein both parts are connected to each other, the first part comprises a recess having a shape matching that of a projection of a device for closing the syringe, and the second part comprises a housing for the closed system transfer device (CSTD) or the cap.

17. The support according to claim 16, wherein the first and second parts are connected to each other by at least one resilient element.

18. A set comprising:

the device according to claim 1 and at least one support for a closed system transfer device (CSTD) or a cap and for use with the said device, comprising a body with a first part and a second part, wherein the first part comprises a recess having a shape matching that of a projection of a device for closing the syringe and the second part comprises a housing for the closed system transfer device (CSTD) or the cap.

19. A system for handling a syringe, comprising the device according to claim 1 and a robotic arm configured to at least handle the syringe during removal and/or insertion of the needle from and/or into the cap, handle the syringe during joint removal of the cap and needle, and handle the syringe during its closure by means of a closed system transfer system (CSTD) or a cap.

20. An automated device for preparing intravenous medication, comprising the device according to claim 1.

21. An automated device for preparing intravenous medication, comprising the system according to claim 19.

* * * * *